(12) United States Patent
Brushey

(10) Patent No.: US 6,676,643 B2
(45) Date of Patent: Jan. 13, 2004

(54) ANESTHESIA CONDUCTION CATHETER

(75) Inventor: Stephen Brushey, Pittsburgh, PA (US)

(73) Assignee: Nicor, Inc., Allison Park, PA (US)

( * ) Notice: Subject to any disclaimer, the term of this patent is extended or adjusted under 35 U.S.C. 154(b) by 0 days.

(21) Appl. No.: 09/816,440

(22) Filed: Mar. 23, 2001

(65) Prior Publication Data

US 2001/0056275 A1 Dec. 27, 2001

Related U.S. Application Data

(60) Provisional application No. 60/191,726, filed on Mar. 24, 2000.

(51) Int. Cl.$^7$ .................................................. A61M 5/00
(52) U.S. Cl. .................. 604/264; 604/246; 604/164.02; 604/164.09; 604/282; 600/500
(58) Field of Search .................................. 604/264, 282, 604/93.01, 164.02, 164.08, 164.09, 246; 600/500

(56) References Cited

U.S. PATENT DOCUMENTS

| 2,118,631 A | * | 5/1938 | Wappler ................. 604/170.02 |
| 3,595,241 A | | 7/1971 | Sheridan |
| 3,757,768 A | | 9/1973 | Kline |

(List continued on next page.)

FOREIGN PATENT DOCUMENTS

| DE | 3400874 | 10/1987 |
| DE | 44 02475 | 3/1996 |
| EP | 0 804 936 | 5/1997 |
| FR | 2 539 298 | 7/1984 |
| FR | 2 622 805 | 5/1989 |
| GB | 2332493 | 6/1999 |
| JP | 04-327857 | 11/1992 |
| WO | WO 92/00113 | 1/1992 |
| WO | WO 94/01160 | 1/1994 |
| WO | WO 96/07445 | 8/1995 |
| WO | WO 96/16690 | 6/1996 |
| WO | WO 96/33761 | 10/1996 |
| WO | WO 97/49447 | 12/1997 |
| WO | WO 01/05210 | 1/2001 |

OTHER PUBLICATIONS

Product Brochure from Arrow Epidural Catheters; Arrow International, Jan. 1999.

*Primary Examiner*—Robin O. Evans
(74) *Attorney, Agent, or Firm*—Thorp, Reed & Armstrong, LLP

(57) ABSTRACT

The present invention provides a catheter which combines the benefits of improved drug dispersion, increased accuracy of placement and kink and collapse resistance. The catheter comprises a flexible cylindrical tube having a proximal portion open at one end and a distal portion, the portions in fluid communication, the distal portion comprising a closed, rounded tip and a diffusion area having at least one opening therein which permits fluid flow, the proximal portion including a proximal tip, and at least one reinforcement member attached at the distal tip and at the proximal tip of the flexible cylindrical tube, with the remainder of the at least one reinforcement member movable within the flexible cylindrical tube. The catheters of the present invention can find use in a variety of local, regional and peripheral pain management applications.

41 Claims, 3 Drawing Sheets

U.S. PATENT DOCUMENTS

| | | | |
|---|---|---|---|
| 3,821,956 A | | 7/1974 | Gordhamer |
| 3,924,632 A | | 12/1975 | Cook |
| 3,938,529 A | * | 2/1976 | Gibbons ................. 604/8 |
| 5,004,456 A | | 4/1991 | Botterbusch et al. |
| 5,066,278 A | | 11/1991 | Hirschberg et al. |
| 5,184,627 A | | 2/1993 | de Toledo |
| 5,201,723 A | | 4/1993 | Quinn |
| 5,209,734 A | * | 5/1993 | Hurley et al. ............. 604/158 |
| 5,267,979 A | | 12/1993 | Appling et al. |
| 5,269,752 A | * | 12/1993 | Bennett .................. 604/28 |
| 5,269,755 A | | 12/1993 | Bodicky |
| 5,356,388 A | | 10/1994 | Sepetka |
| 5,376,083 A | | 12/1994 | Mische |
| 5,405,316 A | * | 4/1995 | Magram ................. 604/8 |
| 5,425,723 A | | 6/1995 | Wang |
| 5,569,219 A | * | 10/1996 | Hakki et al. ............. 604/524 |
| 5,643,228 A | | 7/1997 | Schucart et al. |
| 5,702,372 A | | 12/1997 | Nelson |
| 5,709,874 A | | 1/1998 | Hanson et al. |
| 5,776,111 A | | 7/1998 | Tesio |
| 5,800,407 A | | 9/1998 | Eldor |
| 5,833,652 A | | 11/1998 | Preissman et al. |
| 5,846,216 A | | 12/1998 | Gonzales et al. |
| 5,947,940 A | | 9/1999 | Beisel |

\* cited by examiner

ANESTHESIA CONDUCTION CATHETER

This application claims the benefit of U.S. Provisional Application No. 60/191,726 filed Mar. 24, 2000.

FIELD OF THE INVENTION

This invention relates in general to catheters, and more specifically, to anesthesia conduction catheters, such as epidural catheters and catheters used for local or regional anesthesia and peripheral pain management.

BACKGROUND OF THE INVENTION

Local or regional anesthesia consists of injecting an agent about the nerves thereby producing a loss of sensation in a region or regions of the body. An example of local or regional anesthesia is an epidural block given to women to ease the pain of childbirth.

Peripheral pain management procedures are continuous peripheral nerve blocks which can be categorized into two types depending on the area of the body where the block is introduced. In upper extremity blocks, the majority of the continuous peripheral nerve blocks performed are in the brachial plexus, i.e., the shoulder and neck regions. Such nerve blocks in the area of the brachial plexus include: interscalene block, supraclavicular block and axillary block.

In lower extremity blocks, the majority of the continuous nerve blocks performed are in the lumbar plexus and the celiac plexus, i.e., the hips and waist areas. Nerve blocks performed in the region of the lumbar plexus are: sciatic block, femoral block, lateral femoral block, obturator block, popliteal block, ankle block and lumbar sympathetic block. Nerve blocks performed in the area of the celiac plexus include: the celiac plexus block, which blocks the splanchnic nerve bundle.

Continuous epidural anesthesia is a technique used to relieve acute and chronic pain, in which an anesthesiologist introduces a conduction catheter via an epidural needle into the patient's epidural space between T10 and L4. The catheter is advanced and checked for "flashback" to indicate whether the distal end of the catheter is properly emplaced in the patient, the needle is removed, and anesthesia is administered. The anesthesia blocks nerve impulses from nerves in the T10 (thoracic vertebra number 10) through S5 (sacral vertebra number 5) region.

The most popular epidural catheter currently in use is a closed-end, non-reinforced catheter with three to five side ports. The preference for the closed end catheter with side ports is due to lowered incidences of inadequate analgesia, i.e., improved drug dispersion, and less need for catheter manipulation. However, a significant drawback to using this type of catheter is the lack of reinforcement that makes the catheter prone to collapsing and/or kink formation during use. Kink formation can make proper placement of the catheter difficult.

To avoid the problems of catheter collapse and kinking associated with closed-end catheters, many anesthesiologists prefer to use a reinforced catheter. Reinforcement may come from a variety of sources including the incorporation into the catheter of wire, polymers, metallic ribbons and the like. A major drawback limiting the use of reinforced catheters is that these catheters are open-ended, which may result in the reinforcement, i.e., the wire or metallic ribbon, becoming detached from inside the catheter and presenting a puncture hazard to the patient. Open-ended catheters were also found in at least one study to provide a less even distribution of analgesia than closed-end catheters (See: *Epidural catheters for obstetrics. Terminal hole or lateral eyes? Reg. Anesth.* Nov.–Dec.; 19 (6):378–85, 1994).

A number of inventions have been directed to solving this problem. For example, U.S. Pat. No. 3,757,768 issued to Kline provides an example of a catheter with the helices of a reinforcing spring embedded into the inner wall. Although this catheter can resist collapse of the catheter wall, it may be prone to kink formation because the spring is part of the catheter and cannot relieve torsional stress accumulated from inserting and advancing the catheter into a patient.

U.S. Pat. No. 3,942,632 issued to Cook provides a catheter consisting of an inner core wrapped by a spiraling fiber glass reinforcement surrounded by an outer core. The layered nature of this construction may help prevent catheter wall collapse but may not permit the release of torsional stress and therefore may not make the catheter resistant to kink formation.

U.S. Pat. No. 5,004,456 issued to Botterbosch et al. provides a catheter with a relatively soft distal portion joined to a relatively stiff portion to help prevent catheter wall collapse. This catheter does not provide reinforcement at the distal portion where it may be needed and further does not make any provision for kink resistance.

U.S. Pat. No. 5,947,940 issued to Beisel provides a catheter that is reinforced with a coil made of plastic ribbons. The reinforcing coil is incorporated directly into the catheter's body by being layered between an inner and outer core. The reinforcing coil can be wound less tightly to allow fluid to flow out of side holes in the catheter wall to provide a more even distribution of anesthesia. Although this catheter can provide resistance to catheter wall collapse, the invention of Beisel does not provide for kink resistance because of its construction incorporating the reinforcing coil directly into the catheter. Beisel teaches at col. 4, lines 4–6, that, "(i)t is impossible to terminate the coil short of the side holes since the unsupported, thin polyurethane tube would then kink or collapse and occlude."

Therefore, a need exists in the art for an anesthesia conduction catheter that will provide the benefits of better dispersion of analgesia obtained from the use of closed-end, side port catheters with the kink and collapse resistance encountered in the use of reinforced catheters.

SUMMARY OF THE INVENTION

The present invention provides such a catheter that combines the benefits of improved drug dispersion, increased accuracy of placement, kink resistance and reinforcement.

The present invention provides a catheter comprising, a flexible cylindrical tube having a proximal portion open at one end and a distal portion, the portions in fluid communication, the distal portion comprising a closed, rounded tip and a diffusion area having at least one opening therein which permits fluid flow, the proximal portion including a proximal tip, and at least one reinforcement member attached at the distal tip and at the proximal tip of the flexible cylindrical tube, with the remainder of the at least one reinforcement member movable within the flexible cylindrical tube.

The present invention further provides a method of administering a fluid, the method comprising, inserting into a patient a catheter comprising a flexible cylindrical tube having a proximal portion open at one end and a distal portion, the portions in fluid communication, the distal portion comprising a closed, rounded tip and a diffusion area having at least one opening therethrough which permits fluid flow, the proximal portion including a proximal tip, and at least one reinforcement member attached at the distal tip and at the proximal tip of the flexible cylindrical tube, with the remainder of the at least one reinforcement member movable within the flexible cylindrical tube; connecting the open proximal end of the catheter to a fluid source; and flowing the fluid from the source through the catheter into the patient.

The present invention yet further provides a method of making a catheter, the method comprising, surrounding at least one reinforcement member with a flexible cylindrical tube, the flexible cylindrical tube having a proximal portion open at one end and a distal portion, the portions in fluid communication, the distal portion comprising a closed, rounded tip and a diffusion area having at least one opening therein which permits fluid flow, the proximal portion including a proximal tip; and attaching the at least one reinforcement member at the distal tip and at the proximal tip of the flexible cylindrical tube such that the at least one reinforcement member is movable within the flexible cylindrical tube.

The present invention still further provides a method of managing peripheral pain, the method comprising inserting into a patient a catheter comprising a flexible cylindrical tube having a proximal portion open at one end and a distal portion, the portions in fluid communication, the distal portion comprising a closed, rounded tip and a diffusion area having at least one opening therethrough which permits fluid flow, the proximal portion including a proximal tip, and at least one reinforcement member attached at the distal tip and at the proximal tip of the flexible cylindrical tube, with the remainder of the at least one reinforcement member movable within the flexible cylindrical tube; connecting the open proximal end of the catheter to a pain management fluid source; and flowing the pain management fluid from the source through the catheter into the patient.

The present invention also provides a method of administering a nerve block, the method comprising inserting into a patient a catheter comprising a flexible cylindrical tube having a proximal portion open at one end and a distal portion, the portions in fluid communication, the distal portion comprising a closed, rounded tip and a diffusion area having at least one opening therethrough which permits fluid flow, the proximal portion including a proximal tip, and at least one reinforcement member attached at the distal tip and at the proximal tip of the flexible cylindrical tube, with the remainder of the at least one reinforcement member movable within the flexible cylindrical tube; connecting the open proximal end of the catheter to a nerve block fluid source; and flowing the nerve block fluid from the source through the catheter into the patient.

These and other advantages and benefits of the present invention will be apparent from the Detailed Description of the Invention herein below.

BRIEF DESCRIPTION OF THE FIGURES

The present invention will now be described for the purpose of illustration and not limitation in conjunction with the following figures wherein.

DETAILED DESCRIPTION OF THE INVENTION

The term "patient" generally refers to living humans and/or animals on which the catheter of the present invention may be employed, but may also include cadavers used for training/teaching purposes.

In the following detailed description, the terms "distal" and "proximal" will be used. As used herein, the term "proximal" refers to that region, portion or end of a device or procedure nearest the person using the device or performing the procedure, while the term "distal" refers to that region, portion or end of a device or procedure nearest a patient upon whom the device is being used or the procedure is being performed.

The catheters of the present invention are intended to be utilized in the introduction of fluids, particularly those fluids containing a pharmaceutically active ingredient, such as anesthesia, into a patient in a wide variety of local, regional and peripheral pain management situations. Such situations, include but are not limited to: interscalene blocks; supraclavicular blocks; axillary blocks; sciatic blocks; femoral blocks; lateral femoral blocks; obturator blocks; popliteal blocks; ankle blocks; lumbar sympathetic blocks; and celiac plexus blocks. More than one catheter of the present invention may be used in situations where a temporary block must be administered followed by a longer-term administration of a pharmaceutically active ingredient. Such situations may include, but are not limited to, caesarian section and hernia surgery.

Figure 1:
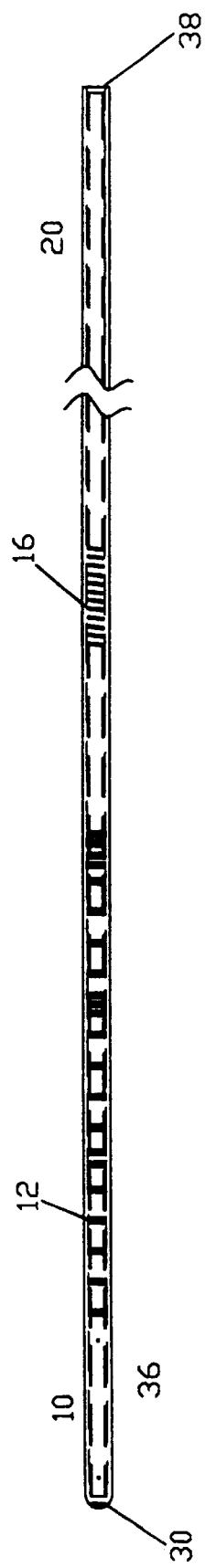
FIG. 1 is a depiction of the catheter of the present invention.

The catheter of the present invention, comprised of closed-end distal portion 10, flashback window 16 and proximal portion 20, is shown in FIG. 1. The catheter of the present invention can preferably be about 12 in. (30.5 cm) to about 36 in. (92 cm) in length and preferably has an inner diameter (I.D.) of between about 0.005 in. (0.127 mm) and about 0.020 in. (0.508 mm) with an outer diameter (OD) of between 28 gauge (G) and 16G, more preferably between 24G and 18G, and most preferably 20G. The thickness of the walls of the catheter of the present invention preferably can be from about 0.003 in. (0.076 mm) to about 0.011 in. (0.279 mm).

Closed-end distal portion 10 is comprised of a distal tip 30 and a diffusion area 36. The diffusion area 36 can be preferably about 0.5 in. (1.27 cm) up to about 20 in. (50.8 cm) in length. The catheter may preferably have one-centimeter marks 12 plus a mark at distal tip 30, as is commonly practiced in the art. Such marks are typically provided on the catheter to allow the anesthesiologist to easily determine how far the catheter has been inserted into a patient and to confirm the catheter's complete removal from a patient. Proximal portion 20 includes a proximal tip 38.

Flashback window 16 can preferably be about 1.0 in. (2.54 cm) in length and is provided to allow the anesthesiologist to visualize blood or cerebrospinal fluid in the catheter upon aspiration, called "flashback" and thereby avoid subarachnoid or intravenous injection of anesthetic. The coils of the reinforcement member 34 in the flashback window 16 region of the catheter of the present invention preferably have a spread of about 0.006 in. (0.152 mm) to about 0.021 in. (0.53 mm) from center to center of the coils.

Figure 2:
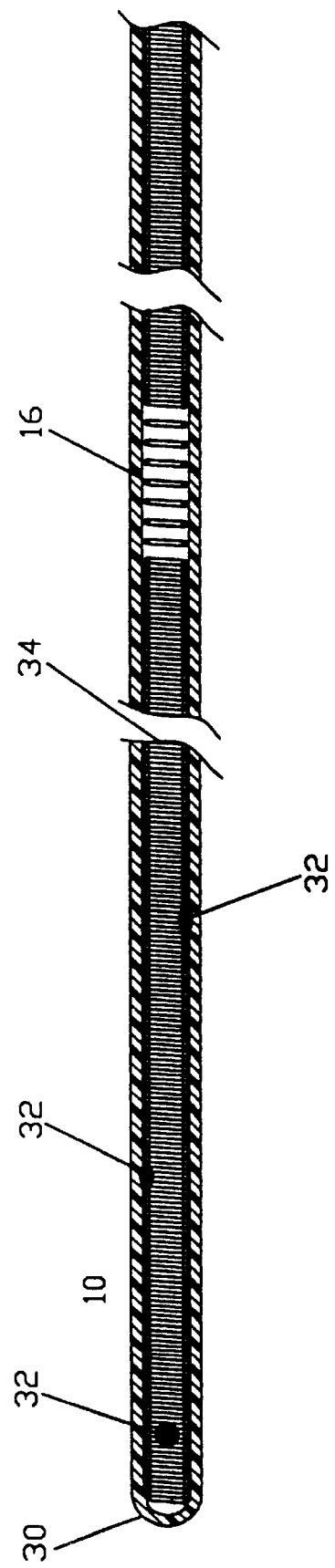
FIG. 2 is an enlarged view of the catheter of FIG. 1 showing the distal portion and flashback window.

FIG. 2 depicts an enlarged view of closed-end distal portion 10 and flashback window 16 of the catheter of FIG. 1. The coils of the reinforcement member 34 in distal portion 10 of the catheter of the present invention preferably have a spread of up to about 0.015 (0.381 mm) from center to center of the coils.

The catheter of the present invention can be made from a variety of sterilizable plastics known to those in the art including, but not limited to, polyamides and copolymers thereof, low density polyethylene, high density polyethylene, polypropylene, polystyrene, polycarbonate, polytetrafluoroethylene, tetrafluoroethylene and fluorinated ethylene propylene. A particularly preferred sterilizable plastic for use in the present invention is nylon polymer. The catheter of the present invention may also be made of polyurethanes. Particularly preferred polyurethanes are those incorporating siloxane available as Elast-Eon™ and described in the following patent applications: PCT/AU91/00270; PCT/AU91/00545; PCT/AU98/00497; PCT/AU97/00619; PCT/AU98/00546; and PCT/AU99/00236.

Figure 3:
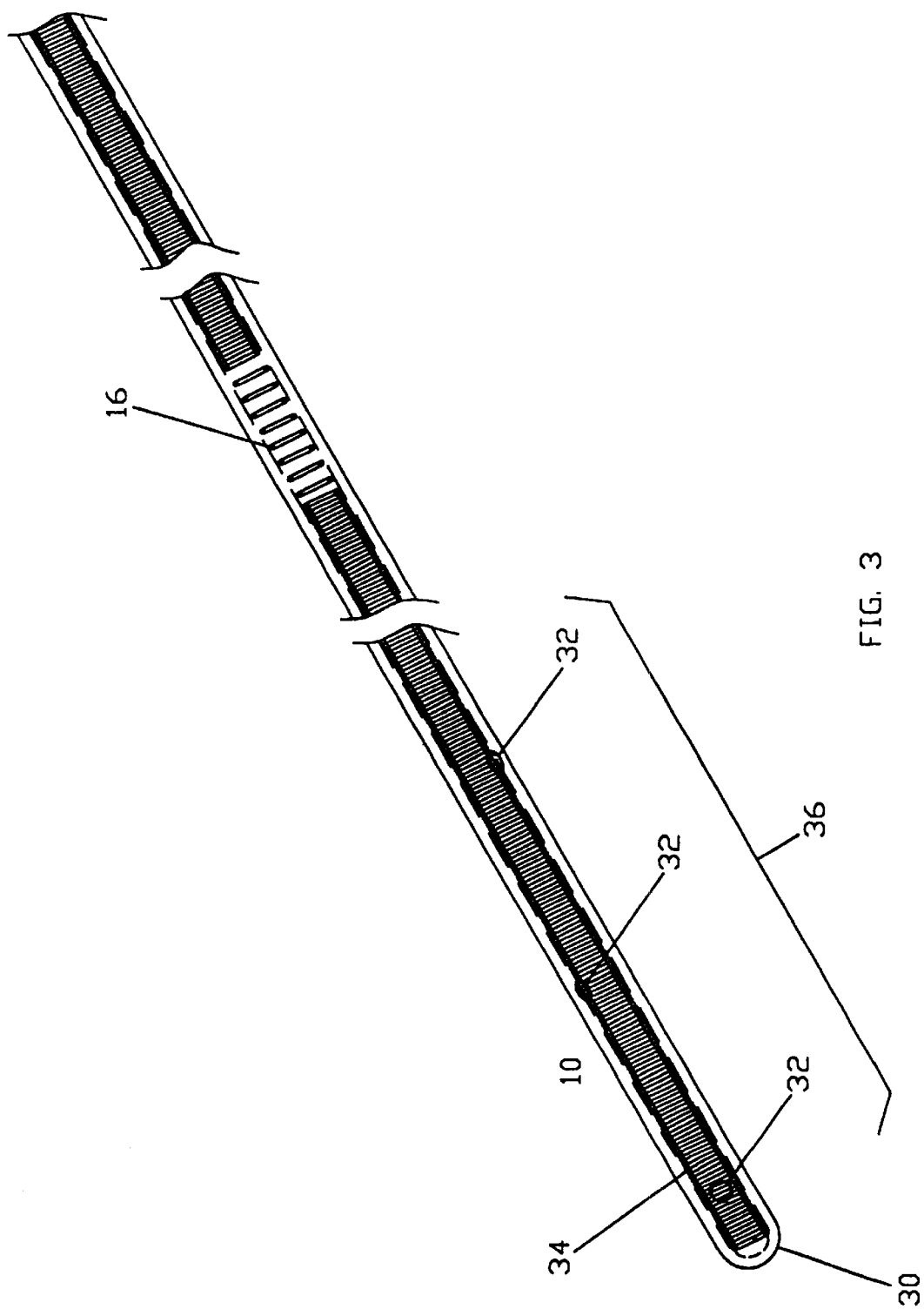
FIG. 3 is an illustration of the distal portion of the catheter of the present invention.

FIG. 3 illustrates the closed-end distal portion 10 of the catheter of FIG. 1. Distal tip 30 is closed and preferably may be rounded, to prevent reinforcement member 34 from becoming dislodged from the catheter of the present invention and thereby posing a puncture hazard to the patient. The combination of a closed, rounded tip and the flexibility of the above-mentioned sterilizable plastics helps prevent venous cannulations and/or dura matter punctures.

Reinforcement member 34 provides collapse resistance for the catheter during use. The reinforcement member 34 is preferably not embedded in, or in any way attached to, the catheter's inner wall, except at the distal tip 30 and the proximal tip 38. The lack of attachment allows the reinforcement member 34 to retain its flexibility by being able to move relatively freely within the catheter's body. The flexibility in turn allows the catheter of the present invention to better resist kinking.

The reinforcement member 34 can be made of a variety of materials, including but not limited to stainless steel, titanium, nickel-titanium and plastic monofilament. A particularly preferred material for use in reinforcement member of the catheter of the present invention is stainless steel, such as #304 wire. Although the reinforcement member of the present invention is depicted herein as a coil, the inventor contemplates that it may take a variety of shapes, including but not limited to strips, ribbons, filaments, braids or mesh.

If radiopacity is desired, the reinforcement member 34 preferably can be made of a radiopaque substance such as steel, titanium or nickel titanium or radiopacity can be conferred by the incorporation of barium, bismuth, etc. in the wall of the catheter. Radiopacity, coupled with fluoroscopy, can facilitate easier placement of the catheter of the present invention as is known by those skilled in the art.

As illustrated in FIG. 3, in one embodiment of the catheter of the present invention the diffusion area 36 may have three openings 32 arranged about 4 mm from each other with the distal most opening being positioned about 5 mm from the distal tip 30. Each opening 32 may preferably be offset from adjacent openings by about 120° circumferentially to provide for a more even distribution of fluid from the catheter. It will readily be apparent to those skilled in the art that a greater number of openings and/or openings in different arrangements can be provided in the catheter of the present invention.

In another embodiment, the openings 32 may be aligned in a straight line or may be in the form of rows. In yet another embodiment, the openings 32 of the catheter of the present invention may be offset from each other by any amount from 0° to 360°. The inventor contemplates that a catheter of the present invention may in some situations have as many as about 100 or more openings in the diffusion area 36. The openings 32 may also be spaced from as little as about 2 mm to as much as about 300 mm apart. Although the catheter of the present invention can be sized to be inserted with 16G to 24G needles as required by the intended application, it can preferably be sized to permit its insertion using a 16G to 21 G epidural needle.

Tests were used to determine the percentage of diffusion area through which flow was achieved and the flow rates of catheters of the present invention, and the results are summarized in Table I. The catheters of the present invention tested varied in the length of diffusion area, i.e., the length of catheter measured from the distal end, through which openings may be drilled and therefore through which fluid flow may occur.

Because there is no standard test for catheter flow rates, the inventor used one test, ISO 10555-3:1996(E), to measure natural, i.e., gravity, flow rates for catheters of the present invention and a pump test to demonstrate achievable flow for the catheter of the present invention using a pump.

Briefly, in the pump test, a Touhy-Borst adapter was attached to the catheter at the proximal end. The catheter was primed with a 3 mL syringe containing distilled water. The outlet line from an appropriate pump (Sorenson or Baxter®), that also contained distilled water was attached to the adapter and the pump was operated. The flow through the diffusion length and the percent diffusion was recorded over a period of 5 to 60 minutes and is reported in Table I.

TABLE I

| Catheter | Length of Diffusion Area in inches (cm) | Percentage of Diffusion Area Through Which Flow Was Achieved | Flow Rate mL/hour | Coil Spread? |
| --- | --- | --- | --- | --- |
| I-A | 1.0 (2.54) | 100 | 0.5 | No |
| I-B | 1.0 (2.54) | 100 | 5.0 | No |
| II-A | 2.0 (5.08) | 78 | 0.5 | No |
| II-B | 2.0 (5.08) | 86 | 5.0 | No |
| III-A | 3.5 (8.89) | 10 | 141.0* | Yes |
| III-B | 3.5 (8.89) | 50 | 38.0* | No |
| IV-A | 5.0 (12.7) | 86 | 5.0 | No |
| IV-B | 5.0 (12.7) | 100 | 125.0 | No |
| V | 7.5 (19.05) | 85 | 5.0 | No |
| VI | 10.2 (25.91) | 70 | 5.0 | No |

*Flow rate measurement made by ISO 10555-3:1996(E).

As can be seen from a review of table I, catheter I provided flow through 100% of its diffusion area at the very slow flow rate of 0.5 mL/hr (I-A) and at 2.0 mL/h (I-B).

Catheter II, with a diffusion area having a length of 2.0 in. (5.08 cm), also showed excellent performance, flowing out of 78% and 86% of the diffusion area, at flow rates of 0.5 mL/hr (II-A) and 5.0 mL/hr (II-B), respectively.

Catheters III-A and B were identical except for the coil being spread in III-A compared to catheter III-B. The data in Table I demonstrate that spreading the coil, as in catheter III-A, resulted in a much higher flow rate, 141 mL/hr, compared to 38 mL/hr for catheter III-B. It should be noted that flow occurred out of only 10% of the diffusion area in catheter III-A compared to 50% in catheter III-B, resulting from the effect of the coil spread in catheter III-A.

Using a diffusion area having a length of 5.0 in. (12.7 cm), resulted in flow occurring out of 86% of the diffusion area at 5.0 mL/hr (IV-A) and out of 100% of the diffusion area at 125 mL/hr (IV-B). This catheter achieved not only a large range of flow rates, but did so with excellent diffusion. As the length of the diffusion area was increased to 7.5 in. (19.05 cm) in catheter V and 10.2 in. (25.91 cm) in catheter VI, flow occurred out of 85 and 70% of the diffusion area, respectively.

The above results demonstrate that catheters of the present invention are capable of flow rates ranging from very low (0.5 mL/hr) to very high (125 mL/hr) with the ability to achieve flow out of 70% to 100% of the diffusion area. The only exceptions to this being catheters III-A and III-B wherein diffusions of 10% and 50% respectively were obtained. However, the inventor contemplates use of catheter III-A in situations where a very high flow rate is required, but where the percentage diffusion is not so important, such as epidural anesthesia.

Although the results summarized in Table I demonstrate that excellent diffusion is obtained in catheters of the present invention having a length of diffusion area as little as 1.0 in. (2.54 cm) to as long an as 10.2 in. (25.91 cm), the inventor contemplates that the length of the diffusion area could be up to about 20 in. (50.8 cm). The results also demonstrate that using catheters of the present invention, control can be achieved over flow rate as well as the diffusion area through which flow occurs.

The conduction catheter of the present invention is intended for administration of local anesthetic or narcotics into intraoperative sites for post-operative pain management and for regional anesthesia outside of the epidural space. Routes of administration may include intraoperative, subcutaneous and percutaneous.

The foregoing illustrations of embodiments of the present invention are offered for the purposes of illustration and not limitation. It will be readily apparent to those skilled in the art that the embodiments described herein may be modified or revised in various ways without departing from the spirit and scope of the invention. The scope of the invention is to be measured by the appended claims.

I claim:

1. A catheter comprising:
   a flexible cylindrical tube having a proximal portion open at one end and a distal portion, said portions in fluid communication, said distal portion comprising a closed, rounded tip and a diffusion area having at least one opening therein which permits fluid flow, said proximal portion including a proximal tip; and
   at least one reinforcement member attached at said distal tip and at said proximal tip of said flexible cylindrical tube, with the remainder of said at least one reinforcement member movable within said flexible cylindrical tube.

2. The catheter of claim 1 with an inner diameter of about 0.005 in. (0.127 mm) to about 0.020 in. (0.508 mm).

3. The catheter of claim 1 with an outer diameter of about 28 gauge to about 16 gauge.

4. The catheter of claim 3 with an outer diameter of about 24 gauge to about 18 gauge.

5. The catheter of claim 4 with an outer diameter of 20 gauge.

6. The catheter of claim 1, wherein the length of said diffusion area is about 0.5 in. (1.27 cm) to about 20 in. (50.8 cm).

7. The catheter of claim 1 further including a window for visualizing flashback.

8. The catheter of claim 1, wherein said flexible cylindrical tube comprises sterilizable plastic.

9. The catheter of claim 8, wherein said sterilizable plastic is selected from the group consisting of polyurethans, low density polyethylene, high density polyethylene, polypropylene, polystyrene, polycarbonate, polytetrafluoroethylene, tetrafluoroethylene, fluorinated ethylene propylene and polyamides.

10. The catheter of claim 8, wherein said sterilizable plastic comprises polyamide and copolymers thereof.

11. The catheter of claim 8, wherein said sterilizable plastic comprises polyurethane which further includes at least one siloxane.

12. The catheter of claim 1, wherein said at least one reinforcement member is made from a material selected from the group consisting of stainless steel, titanium, nickel-titanium and plastic filament.

13. The catheter of claim 1, wherein the shape of said at least one reinforcement member is selected from the group consisting of coil, strip, ribbon, filament, braid or mesh.

14. The catheter of claim 1, wherein the shape of said at least one reinforcement member comprises a coil.

15. The catheter of claim 14 with said coil comprising stainless steel wire.

16. The catheter of claim 14 with said coil having a spread of up to about 0.01 5 in. (0.381 mm) from center to center of said coil.

17. The catheter of claim 1 having 2 to about 100 openings in said diffusion area.

18. The catheter of claim 17 having 3 to about 13 openings in said diffusion area.

19. The catheter of claim 17, wherein said openings are offset about 0°–360° circumferentially from adjacent said openings.

20. The catheter of claim 17 with said openings forming a row.

21. The catheter of claim 17 with said openings spaced about 2 to about 300 mm from adjacent said openings.

22. A method of making a catheter, said method comprising:
   surrounding at least one reinforcement member with a flexible cylindrical tube, said flexible cylindrical tube having a proximal portion open at one end and a distal portion, said portions in fluid communication, said distal portion comprising a closed, rounded tip and a diffusion area having at least one opening therein which permits fluid flow, said proximal portion including a proximal tip; and
   attaching said at least one reinforcement member at said distal tip and at said proximal tip of said flexible cylindrical tube such that said at least one reinforcement member is movable within said flexible cylindrical tube.

23. The method of claim 22, wherein the shape of said at least one reinforcement member comprises a coil.

24. The method of claim 23, wherein said coil comprises stainless steel wire.

25. The method of claim 22, wherein said catheter comprises 2 to about 100 openings in said diffusion area.

26. The method of claim 25, wherein said catheter comprises 3 to about 13 openings in said diffusion area.

27. The method of claim 25, wherein said openings are offset about 0°–360° circumferentially from adjacent said openings.

28. The method of claim 25, wherein said openings form a row.

29. The method of claim 22, wherein said catheter has an inner diameter of about 0.005 in. (0.127 mm) to about 0.020 in. (0.508 mm).

30. The method of claim 22, wherein said catheter has an outer diameter of about 28 gauge to about 16 gauge.

31. The method of claim 30, wherein said catheter has an outer diameter of about 24 gauge to about 18 gauge.

32. The method of claim 31, wherein said catheter has an outer diameter of 20 gauge.

33. The method of claim 22, wherein the length of said diffusion area is about 0.5 in. (1.27 cm) to about 20 in. (50.8 cm).

34. The method of claim 22, wherein said catheter further includes a window for visualizing flashback.

35. The method of claim 22, wherein said catheter comprises sterilizable plastic.

36. The method of claim 35, wherein said sterilizable plastic is selected from the group consisting of polyurethanes, low density polyethylene, high density polyethylene, polypropylene, polystyrene, polycarbonate, polytetrafluoroethylene, tetrafluoroethylene, fluorinated ethylene propylene and polyamides.

37. The method of claim 35, wherein said sterilizable plastic comprises polyamide and copolymers thereof.

38. The method of claim 35, wherein said sterilizable plastic comprises polyurethane which further includes at least one siloxane.

39. The method of claim 22, wherein said at least one reinforcement member is made from a material selected from the group consisting of stainless steel, titanium and nickel-titanium.

40. The method of claim 22, wherein the shape of said at least one reinforcement member is selected from the group consisting of coil, strip, ribbon, filament, braid or mesh.

41. The method of claim 25, wherein said openings are spaced about 2 to about 300 mm from adjacent said openings.

* * * * *

UNITED STATES PATENT AND TRADEMARK OFFICE
CERTIFICATE OF CORRECTION

PATENT NO. : 6,676,643 B2
DATED : January 13, 2004
INVENTOR(S) : Brushey

It is certified that error appears in the above-identified patent and that said Letters Patent is hereby corrected as shown below:

Title page,
Item [73], Assignee, delete "Nicor, Inc." and insert therefor -- Micor, Inc. --.

Column 1,
Line 49, delete"closed end" and insert therefore -- closed-end --.

Column 6,
Line 2, delete "21 G" and insert therefore -- 21G --.
Line 42, delete "table I" and insert therefore -- Table I --.
Line 44, delete "mL/h" and insert therefore -- mL/hr --.
Line 64, delete "85" and insert therefore -- 85% --.

Column 7,
Line 12, delete "an".

Signed and Sealed this

Third Day of August, 2004

JON W. DUDAS
*Acting Director of the United States Patent and Trademark Office*